(12) United States Patent
Razian

(10) Patent No.: US 7,749,274 B2
(45) Date of Patent: Jul. 6, 2010

(54) INTERVERTEBRAL CAGE WITH MEDIAL FIXING PLATE

(76) Inventor: Hassan Razian, 55, Avenue du General de Gaulle, L'Hay les Roses, F-94240 (FR)

( * ) Notice: Subject to any disclaimer, the term of this patent is extended or adjusted under 35 U.S.C. 154(b) by 1455 days.

(21) Appl. No.: 10/534,865

(22) PCT Filed: Oct. 24, 2003

(86) PCT No.: PCT/FR03/03149

§ 371 (c)(1),
(2), (4) Date: May 12, 2005

(87) PCT Pub. No.: WO2004/043306

PCT Pub. Date: May 27, 2004

(65) Prior Publication Data

US 2005/0283236 A1    Dec. 22, 2005

(30) Foreign Application Priority Data

Nov. 12, 2002  (FR)  .................................. 02 14080

(51) Int. Cl.
*A61F 2/44* (2006.01)
(52) U.S. Cl. .................................................. 623/17.16
(58) Field of Classification Search .... 623/17.11–17.16
See application file for complete search history.

(56) References Cited

U.S. PATENT DOCUMENTS

| | | | |
|---|---|---|---|
| 4,711,234 A * | 12/1987 | Vives et al. | 606/60 |
| 5,683,394 A | 11/1997 | Rinner | |
| 6,102,949 A | 8/2000 | Biedermann et al. | |
| 6,371,987 B1 | 4/2002 | Weiland et al. | |
| 6,770,096 B2 * | 8/2004 | Bolger et al. | 623/17.16 |
| 2005/0261773 A1 * | 11/2005 | Ferree | 623/17.16 |

FOREIGN PATENT DOCUMENTS

DE        198 16 832        1/2000

* cited by examiner

*Primary Examiner*—David J Isabella
*Assistant Examiner*—Ann Schillinger
(74) *Attorney, Agent, or Firm*—Young & Thompson

(57) ABSTRACT

An intervertebral cage for treating degeneration of the spine includes a block, an anchor member with a pivot and two blades secured to the pivot, a device for mounting the pivot to turn relative to the block and a hole in the block, a slot in the block, where the slot shares a common portion with the hole for containing the pivot, and a device for associating the pivot in rotation with the block in the common portion in such a manner that when the pivot is turned, the anchor member takes up a first position in which the blade is fully contained in the slot and a second position in which a portion of the end of the blade emerges from the slot.

2 Claims, 3 Drawing Sheets

INTERVERTEBRAL CAGE WITH MEDIAL FIXING PLATE

FIELD OF THE INVENTION

The present invention relates to intervertebral cages which find a particularly advantageous, but non-exclusive, application in treating degeneration of the spine, and it relates more particularly to an improvement to already-known intervertebral cages.

BACKGROUND OF THE INVENTION

Intervertebral cages, in particular for treating degeneration of the spine, are already known. For example, one such cage is described in document EP-A-1 104 662. It essentially comprises a disk-shaped spacer having two substantially plane and parallel opposite base faces and a side wall uniting the two base faces. The spacer is suitable for being placed between the facing faces of two vertebral bodies respectively of two consecutive vertebrae, to replace the damaged disk situated between those two vertebrae, the two base faces of the spacer being placed in contact with the vertebral bodies. The spacer may also have an open cavity in which it is possible to place a bone graft or the like in order to bond together the two vertebral bodies by osteosynthesis. The cage also includes at least one member having two chamfered opposite ends, and means for moving the member relative to a first of two side wall portions so that the member can take up two positions, a first position in which the member is situated entirely within the space lying between the first and second planes containing the two base faces of the spacer, and a second position in which the two opposite ends of the member emerge from either side of said space.

In the above-described cages, the anchor member is associated with a spacer on one of the faces thereof. Such an embodiment requires a certain number of elements in order to make it relatively easy to turn the member relative to the spacer. In an attempt to minimize the number of such elements, a solution has been tried that consists in positioning the anchor member substantially in the middle portion of the spacer, as for example in the embodiment described in WO 01/01894. The solution adopted for making that cage has nevertheless not given full satisfaction, essentially because the way the member is integrated in the middle portion of the spacer is still too complex and makes it relatively complicated to implant the cage between two vertebrae.

In an attempt to mitigate the above-mentioned drawbacks, an intervertebral cage has also been made as described, for example, in U.S. Pat. No. 6,371,987 B1. That cage satisfies in general manner the requirements of practitioners, but it still presents drawbacks, in particular for its manufacture.

SUMMARY OF THE INVENTION

An object of the present invention is thus to provide an improvement to intervertebral cages of the above-defined type, presenting a structure that is easier to make and to assemble, and making it much easier to implant the cage between two vertebrae.

More precisely, the present invention provides an intervertebral cage for treating degeneration of the spine and suitable for being interposed between two consecutive vertebrae, the cage comprising:

a block;

at least one anchor member comprising a pivot defining a first axis of rotation, and at least one blade secured to said pivot and occupying substantially a first plane making a non-zero angle $\alpha$ relative to said first axis; and means for mounting the pivot to turn relative to said block, said means comprising a hole made in the block along a second axis, a slot made in the block substantially in a second plane making an angle $\gamma$ substantially equal to the angle $\alpha$ relative to the second axis, the slot also being made in such a manner that, together with the hole, it has a common portion suitable for containing the pivot, and means for associating the pivot to turn relative to the block when the pivot is in position in said common portion and in such a manner that when, in said position, the pivot is turned through a given amplitude relative to the block, the anchor member is suitable for taking up at least a first position and a second position, the first position being that in which the blade is fully contained within the slot, and the second position being that in which a portion of the end of the blade emerges from said slot;

the cage being characterized by the fact that for the pivot being constituted by a second rotary shaft having the first axis as its axis, the means for associating the pivot in rotation with the block comprises a second bearing that is open towards the opening of said slot situated in the surface of the block, said open second bearing being made in the margin of said common portion in such a manner as to be centered on said second axis, the diameters of the open second bearing and of the second rotary shaft being substantially equal, the diameter of the second rotary shaft and of the open second bearing being greater than the minimum diametral dimension of the cross-section of the hole.

BRIEF DESCRIPTION OF THE DRAWINGS

Other characteristics and advantages of the invention appear from the following description given by way of non-limiting illustration with reference to the accompanying drawings, in which.

DETAILED DESCRIPTION OF EMBODIMENTS

It is specified that in the figures the same references are used to designate elements that are the same regardless of the figure in which they appear and regardless of the way in which said elements are shown.

Similarly, if elements are not specifically referenced in one of the figures, their references can easily be found by referring to another figure.

The Applicant also seeks to specify that the figures show three embodiments of the invention, but that other embodiments can also exist that satisfy the definition of the invention.

The Applicant further specifies that when, in the definition of the invention, its subject matter is stated to comprise "at least one" element having some given function, the embodiment described may have a plurality of such elements.

It is also specified that if the embodiment of the invention as shown has a plurality of elements of identical function and if in the description it is not specified that the invention must necessarily have some particular number of these elements, then the invention can be defined as comprising "at least one" of said elements.

The present invention relates to an improved intervertebral cage serving in particular for treating degeneration of the spine.

Figure 1:
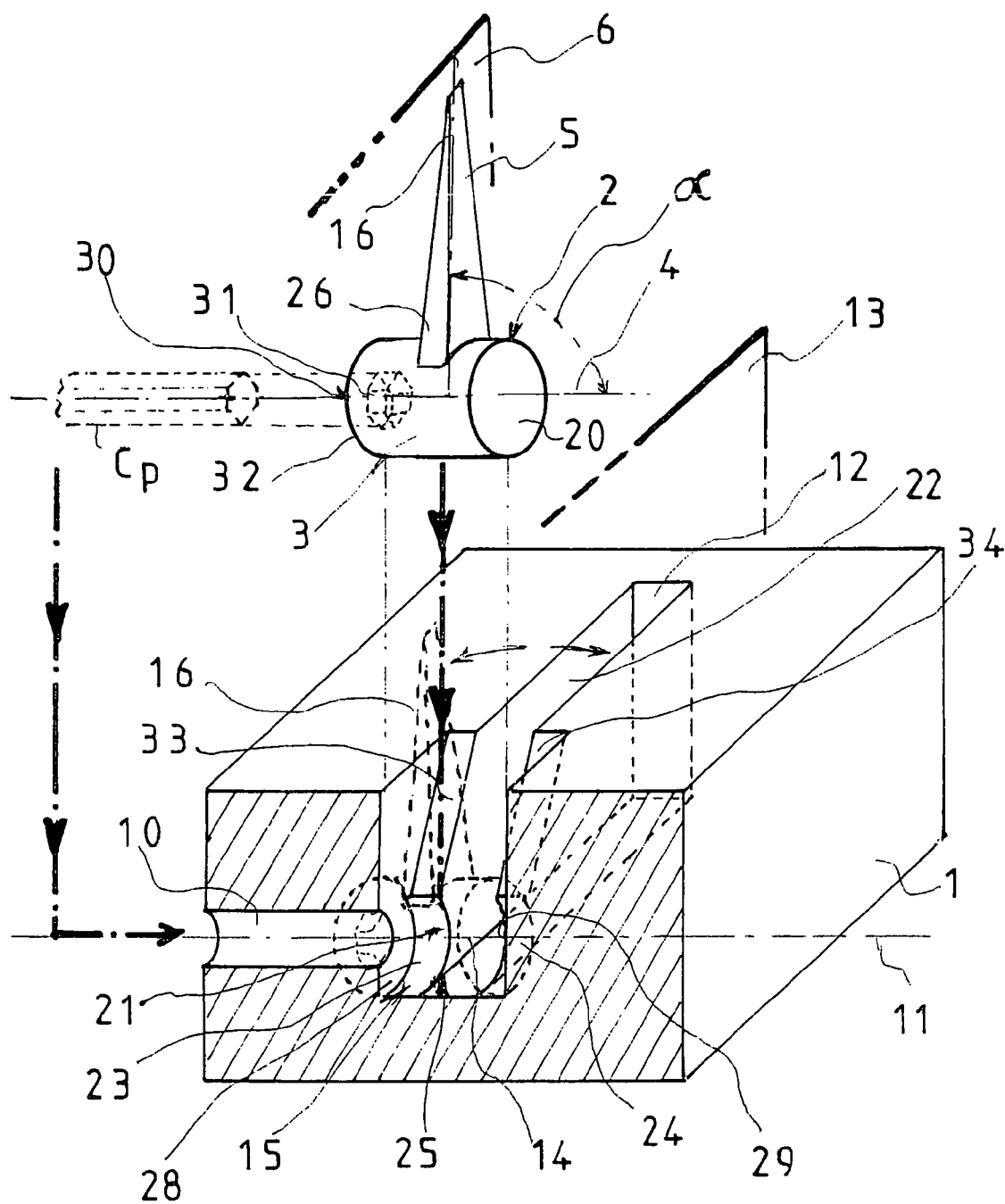
FIG. 1 is an exploded perspective view in half-section showing diagrammatically a first embodiment of the intervertebral cage of the invention.

FIG. 1 is a functional diagram showing an embodiment of an intervertebral cage of the invention.

The cage comprises a block 1 of a shape similar to that of a rectangular parallelepiped, or more generally capable of being inscribed in a rectangular parallelepiped. In particular, it could have the shape shown in FIG. 2.

Figure 2:
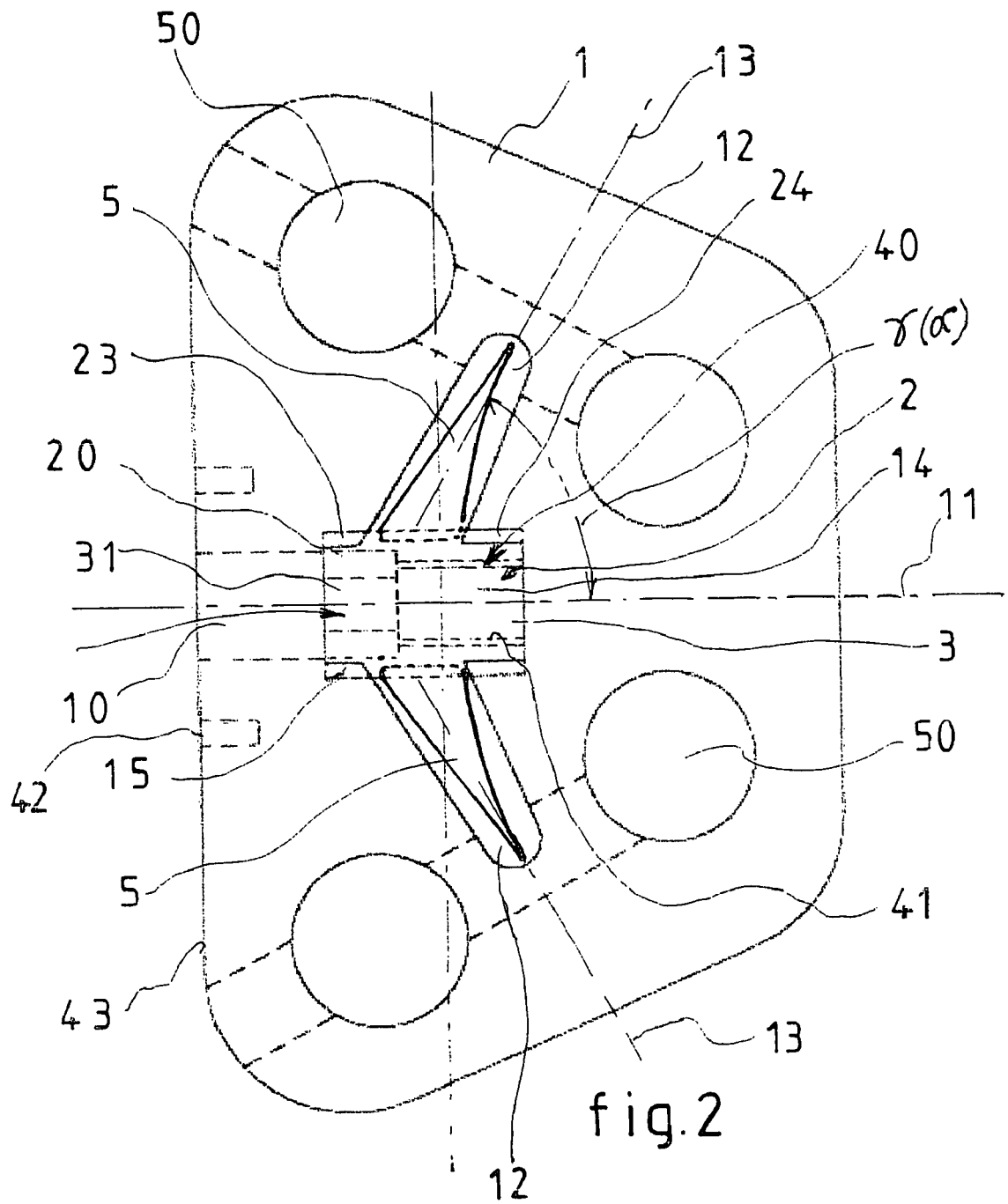
FIG. 2 is a plan view of a preferred, second embodiment of the cage of the invention.
Figure 3:
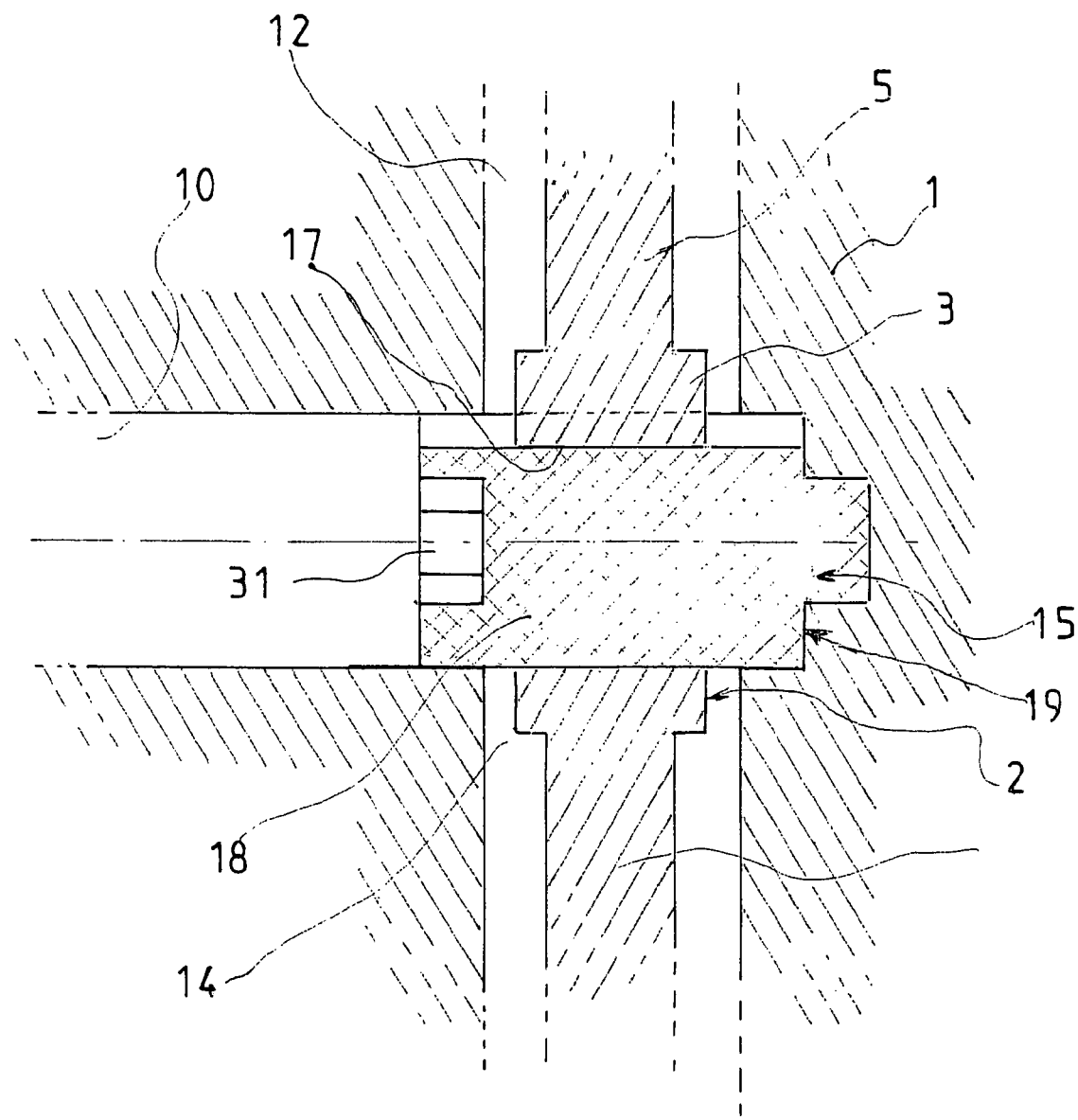
FIG. 3 is a fragmentary section view of a possible third embodiment of the cage of the invention.

The cage also includes at least one anchor member 2 having a pivot 3 defining a first axis of rotation 4, and at least one blade 5 secured to the pivot 3 and occupying substantially a first plane 6 making a non-zero angle α with the first axis 4, and advantageously two blades as in the embodiments of FIGS. 2 and 3, for anchoring in the two consecutive vertebrae between which the cage is to be implanted.

The cage includes means for mounting the pivot 3 to pivot relative to the block 1, said means comprising: a hole 10 formed in the block on a second axis 11; a slot 12 made in the block occupying substantially a second plane 13 making an angle γ relative to the second axis 11 that is substantially equal to the angle α, the slot 12 also being made in such a manner that, together with the hole 10, it has a common portion 14 suitable for containing the pivot 3; and means 15 for associating the pivot 3 to turn relative to the block 1 when the pivot is positioned in the common portion 14 and in such a manner that when, in this position, the pivot is turned through a given amplitude relative to the block, the anchor member 2 is suitable for taking up at least a first position and a second position, the first position being that in which the blade 5 is completely contained within the slot 12, and the second position being that in which a portion 16 of the end of the member emerges from the slot.

It is specified that in the embodiment of FIG. 1, the anchor member 2 has only one blade 5. In this configuration, the slot 12 may have the shape as shown in FIG. 1. When the anchor member has two blades in a substantially symmetrical configuration, as in the embodiment of FIG. 2, each blade corresponds to at least one slot 12, as shown in FIG. 1. However, in an embodiment that is advantageous, in particular in terms of machining, the two slots corresponding to the two blades are implemented as a single slot passing right through the block 1 as shown in FIG. 2, this configuration also enabling the anchor member to pivot in either direction in order to achieve the results specified below.

In the embodiment shown in FIG. 1, the angles α and γ are substantially equal to 90°, but they are advantageously selected to be smaller in value, e.g. 70°, so as to enable the cage to be retained by the two vertebrae.

In a possible embodiment, as shown in FIG. 3, the pivot 3 is constituted by a hollow first bearing 17, advantageously in the form of a sleeve having an inside wall that is circularly cylindrical. Under such circumstances, the means 15 for associating the pivot 3 in rotation relative to the block 1 comprise a first rotary shaft 18 mounted with rotary indexing means in the hollow first bearing 17, and means 19 for mounting the first rotary shaft 18 in co-operation with the block 1. As shown in FIG. 3, these means 19 may be constituted by a key-type assembly, e.g. secured to the pivot 3 and co-operating with a corresponding groove formed in the first rotary shaft 18. In addition, this first rotary shaft 18 has a cross-section that is substantially complementary to that of the hole 10 so as to enable it to be inserted therein as a relatively tight fit.

This embodiment is relatively advantageous both in terms of structure and for implanting the cage.

Nevertheless, compared with the embodiment of FIG. 3, an embodiment of the kind shown in FIGS. 1 and 2 is preferred since it presents two essential advantages compared with the embodiment of FIG. 3, namely that it requires fewer component parts, two instead of three, and that the parts can be assembled together very easily, and automatically.

In the embodiments of FIGS. 1 and 2, the pivot 3 is constituted by a second rotary shaft 20 having the first axis 4 as its axis, and the means 15 for associating the pivot in rotation with the block comprise a second bearing 21 that is open towards the opening 22 of the slot 12 situated in the surface of the block 1, the open second bearing being made in the margin of the common portion 14 so as to be centered on the second axis 11, the diameters of the open second bearing 21 and of the second rotary shaft 20 being substantially equal.

Advantageously, the diameter of the second rotary shaft 20 and of the open second bearing 21 is greater than the minimum diametral dimension of the cross-section of the hole 10. In this way, when the pivot is placed in the open second bearing 21, it is held between the two shoulders formed by the wall 29 of the slot 12 and by the edge 28 at the end of the hole 10 that opens out into the common portion 14.

Preferably, the open second bearing 21 is constituted by two open cylindrical surfaces 23 and 24 separated by an empty space 25 of a width not less than the maximum thickness of the blade 5 at its portion 26 that is secured to the pivot 3.

In an advantageous embodiment, this open second bearing 21 is a retention bearing. Under such circumstances, at least one of the two open cylindrical surface 23 and 24, and advantageously both of them, is defined over an angle of more than 180°, but very little more than 180°.

Furthermore, in the embodiment described above, the two open cylindrical surfaces 23 and 24 are connected to the surface of the block 1 into which the slots 12 open out by two respective ramps 33 and 34 that form two guide ramps for inserting the second rotary shaft 20 into the hollow second bearing 21. In FIG. 1, the two ramps 33 and 34 (which ramps are naturally to be found in symmetrical manner in the other half to the block 1 (not shown)) are drawn forming a funnel having an angle at the apex that is relatively large in order to emphasize the guidance function of the two ramps. However, in practice, and as shown in FIG. 1, this angle at the apex has a value that is very small.

The intervertebral cage further includes means 30 for turning the pivot 3 about the second axis 11 so that the anchor member 2 is suitable for taking up its first and second positions as defined above.

By way of example, the means 30 are constituted by a socket 31 of polygonal cross-section formed in the face 32 of the second rotary shaft 20 that faces the hole 10 when the second rotary shaft 20 is mounted to pivot in the open second bearing 21, this socket 31 being substantially centered on the first axis 4 and being of cross-section that is smaller than that of the hole 10.

In an advantageous embodiment, the intervertebral cage has an orifice 40 with tapping 41 made in the wall thereof, which orifice is made in the second rotary shaft 20, being centered on the first axis 4 and opening out into the end of the socket 31, the diameter of the tapped orifice 40 being smaller than the cross-section of said hollow housing, and means 42 for indexing the position of an ancillary relative to the block 1 and made on the face 43 of the block into which the hole 10 opens out. By way of example, these means 42 are constituted by two or more notches, it being understood that the ancillary needs to have studs suitable for being engaged in the notches 42 and a threaded rod suitable for screw engagement in the tapped orifice 40 when the studs are engaged in the notches.

The elements of the intervertebral cage as described above with reference more particularly to FIGS. 1 and 2 are assembled together as described below and the cage is used as follows:

Firstly, it is specified that the block 1 and the anchor member 2 are machined in conventional manner to have the structural characteristics described above. Once these two elements have been made, the anchor member 2 is presented via the pivot 20 in the funnel formed by the ramps 33 and 34. It is pushed down under force until the pivot snaps into the open second bearing 21. Once the pivot has taken up position in this open second bearing, it is securely held by the two shoulders 28 and 29 and by the two open cylindrical surfaces 23 and 24 that are defined over an angle of more than 180°.

Once the anchor member 2 has taken up a position as shown in dashed lines in FIG. 1, which corresponds to the second above-defined position, e.g. under drive from a polygonal section key Cp drawn in dashed lines in FIG. 1 and complementary to the socket 31, being inserted into said socket via the hole 10, the anchor member 2 is taken to its first position as shown in FIG. 2. In this position, both blades 5 of the member are fully retracted, being contained in full within the slots 12.

In known manner, the practitioner then inserts the cage of the invention between two consecutive vertebrae as a replacement for the intervertebral disk, the anchor member being in its first position. To do this, the practitioner makes use of the above-described ancillary.

By means of the polygonal section key Cp inserted in the socket 31 via the hole 10, the practitioner then causes the anchor member to go from its first position to its second position, the end portions 16 of the blades 5 then digging into the bony portions of the two vertebrae in the same manner as applies to intervertebral cages of the same type in the prior art.

In order to define the second position of the anchor member and contribute to proper placing of the cage by the practitioner, the cage may further include, for example, a first snap-fastener constituted in conventional manner by a stud made on a pivot and by a groove made in the block 1 that co-operate one in the other, e.g. by deformation, once the anchor member reaches its second position. The cage may also have a second snap-fastener for defining a first position of the anchor member, and the same stud can indeed be common to both snap-fasteners.

It is specified that the cage of the invention may also have characteristics other than those defined above, for example holes 50 for receiving bone grafts such as those shown in FIG. 2. These other characteristics are not described herein since they do not come within the field of the present invention.

The invention claimed is:

1. An intervertebral cage for treating degeneration of the spine and suitable for being interposed between two consecutive vertebrae, the cage comprising:
    a block;
    at least one anchor member comprising a pivot defining a first axis of rotation, and at least one blade secured to said pivot and occupying substantially a first plane making a non-zero angle α relative to said first axis;
    means for mounting the pivot to turn relative to said block, said means comprising a hole in the block along a second axis, a slot in the block substantially in a second plane making an angle γ substantially equal to the angle α relative to the second axis, the slot and the hole having a common portion suitable for containing the pivot, and means for associating the pivot to turn relative to the block when the pivot is in position in said common portion and in such a manner that when, in said position, the pivot is turned through a given amplitude relative to the block, the anchor member is suitable for taking up at least a first position and a second position, the first position being that in which the blade is fully contained within the slot, and the second position being that in which a portion of the end of the blade emerges from said slot;
    the pivot includes a second rotary shaft having the first axis as its axis, the means for associating the pivot to turn relative to the block comprises a second bearing that is open towards an opening of said slot situated in the surface of the block, said second bearing being in said common portion so as to be centered on said second axis, diameters of the second bearing and of the second rotary shaft being substantially equal, the diameters of the second rotary shaft and of the second bearing being greater than a minimum diameter of the cross-section of the hole; and
    further comprising means for turning said pivot about said second axis in such a manner that said anchor member is suitable for taking up said first position and said second position,
    wherein the means for turning said pivot about said second axis comprise a socket of polygonal cross-section made in the face of the second rotary shaft that faces the hole when said second rotary shaft is mounted to rotate in the open second bearing, said socket being centered substantially on said first axis and being of cross-section smaller than that of said hole.

2. The intervertebral cage according to claim 1, further comprising an orifice having tapping, said orifice being formed in the second rotary shaft being centered on the first axis and opening out into the end of said hollow recess, the diameter of said tapped orifice being less than the cross-section of said socket, and means for indexing the position of an ancillary relative to the block formed in the face of the block into which said hole opens out.

* * * * *